United States Patent [19]

Tuxill

[11] Patent Number: 5,027,811

[45] Date of Patent: Jul. 2, 1991

[54] TRACHEOSTOMY CHAMBER HAVING ADAPTER FOR SUCTION CAPABILITY

[76] Inventor: Judith D. Tuxill, 4399 Plantation Blvd., Liverpool, N.Y. 13090

[21] Appl. No.: 541,928

[22] Filed: Jun. 4, 1990

[51] Int. Cl.[5] .................... A61M 16/00; A61M 16/06

[52] U.S. Cl. .................... 128/207.14; 128/207.17

[58] Field of Search .................. 128/207.14, DIG. 26, 128/207.17, 207.15, 911, 912, 206.22

[56] References Cited

U.S. PATENT DOCUMENTS

| | | | |
|---|---|---|---|
| 3,236,236 | 2/1966 | Hudson | 128/207.17 |
| 4,274,406 | 6/1981 | Bartholomew | 128/912 |
| 4,328,797 | 5/1982 | Rollins III et al. | 128/912 |
| 4,462,400 | 7/1984 | Simons et al. | 128/207.17 |
| 4,598,705 | 7/1986 | Lichtenberger | 128/207.14 |
| 4,649,913 | 3/1987 | Watson | 128/207.17 |
| 4,722,334 | 2/1988 | Blackmer et al. | 128/203.16 |

*Primary Examiner*—Edgar S. Burr
*Assistant Examiner*—Stephen R. Funk
*Attorney, Agent, or Firm*—J. Gibson Semmes

[57] ABSTRACT

A device which adapts to the neck of a patient who has undergone a tracheostomy. It is useful in supplying humidification and oxygenation upon inhalation and to exhaust the outgoing exhalation gases and secretions upon exhalation. It is characterized as a tracheostomy bubble and has front and rear barriers which remain in spaced relation to each other, irrespective of the patient's breathing.

2 Claims, 1 Drawing Sheet

TRACHEOSTOMY CHAMBER HAVING ADAPTER FOR SUCTION CAPABILITY

BACKGROUND OF INVENTION

This invention relates to the art of tracheostomy devices comprising an external chamber which surrounds a tracheostomy tube leading outwardly from a patient's trachea, to facilitate breathing through the lungs wherein the natural "windpipe" function has failed or wherein a bypass of the upper trachea has been required to sustain a normal breathing function.

In the use of most tracheostomy devices the care-giver is exposed to patient secretions which oftentimes carry harmful bacteria. This invention has as one objective the limitation of the care-giver's exposure to such fluid and secretions which develop in the course of a patient's breathing/coughing as when wearing a tracheostomy device. Another objective is to maintain as clean as possible, the environment around the patient's incision in the neck and trachea. A further objective is to increase assurance that the patient's respiratory tract receives the appropriate humidification and oxygenation.

The present tracheostomy chamber device meets these objectives.

SUMMARY OF INVENTION

The device consists primarily of a base member which forms a curvilinear rear wall to which is hermetically sealed a forwardly extending bubble portion. A tracheostomy tube channel is defined in the rear barrier of the device, the same having spaced connection from the front barrier which likewise defines an exhalation outlet and an aerosol inlet. A suction adapter is located at the terminus of the lower portion of the front barrier and adjustable strap means are provided to secure the device to the neck of the patient.

This medical device provides air or oxygen having attendant humidification, which is delivered via an aerosol input connection. This device actually supplies containment of condensate humidification condensate as well as inadvertently expectorated secretions which may originate from the tracheostomy opening. At the lowest point of the chamber an adapter is provided which is suction serviced, allowing liquid and secretions to be suctioned out, without exposing the care-giver. It also protects the patient from much of the wetness and secretions that may build up around other non-enclosed devices.

As a result of the chamber's unique construction, there is more likelihood that the patient receives the prescribed oxygenation/humidification.

DESCRIPTION OF THE PRIOR ART

Tracheotomy devices combining respirator and a trachea tube have been created in the past. U.S. Pat. No. 3,461,877 to Morch represents perhaps the earliest development of a rather antiquated tracheotomy combination for use with a respirator. This patent teaches a swivel connection, replacing back threading method, to prevent dislodging the tracheostomy from the patient.

U.S. Pat. No. 4,494,252 to Chaoui and U.S. Pat. No. 4,538,607 to Saul both illustrate inhalation and exhalation valves, the former using two separate conduits, while the latter defines a permanently installed tracheostomy valve. Neither suggests removal of the secretions and wetness through a lower valve adapter nor a means to enclose the patient's inserted tube. The bandage illustrated in U.S. Pat. No. 3,920,009 to Olsen provides a fibrous material to collect particles and bacteria in such a way as to cause substantial resistance to the inhaled air. This does not suggest a chamber enclosuring of the tracheostomy tube nor the protection it provides to the care-giver and patient from contaminated wetness and secretions that may be infectious.

U.S. Pat. No. 4,272,406 to Bartholomew adopts a related configuration of prosthesis as does Hudson U.S. Pat. No. 3,236,236, but neither comprise the unique rear and frontal walls that enclose the trachea, minimizing wetness or secretion exposure, securing the tracheostomy tube to the administration device, providing the likelihood that the patient will inhale the oxygen/humidity mixture.

DESCRIPTION OF PREFERRED EMBODIMENTS

Figure 1:
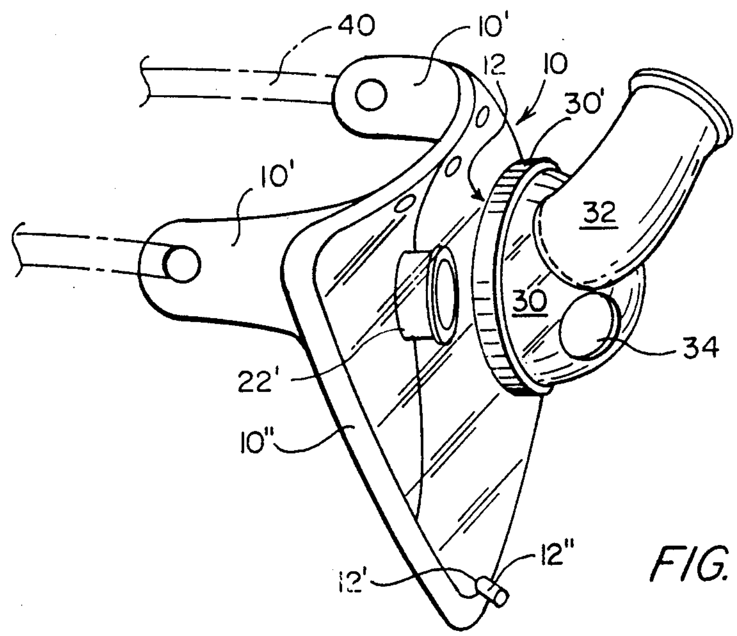
FIG. 1 is a view in perspective of the invention defined herein.
Figure 2:
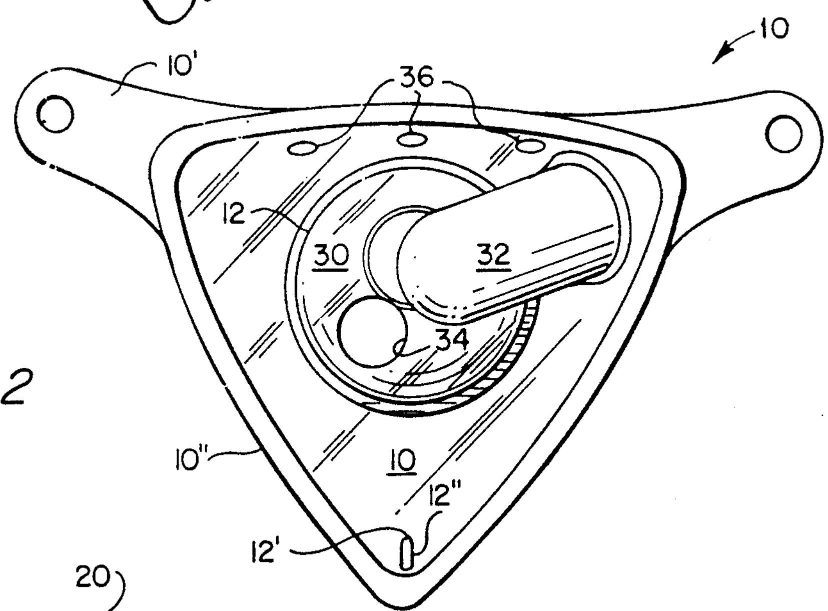
FIG. 2 is a front view of the invention shown in FIG. 1.
Figure 3:
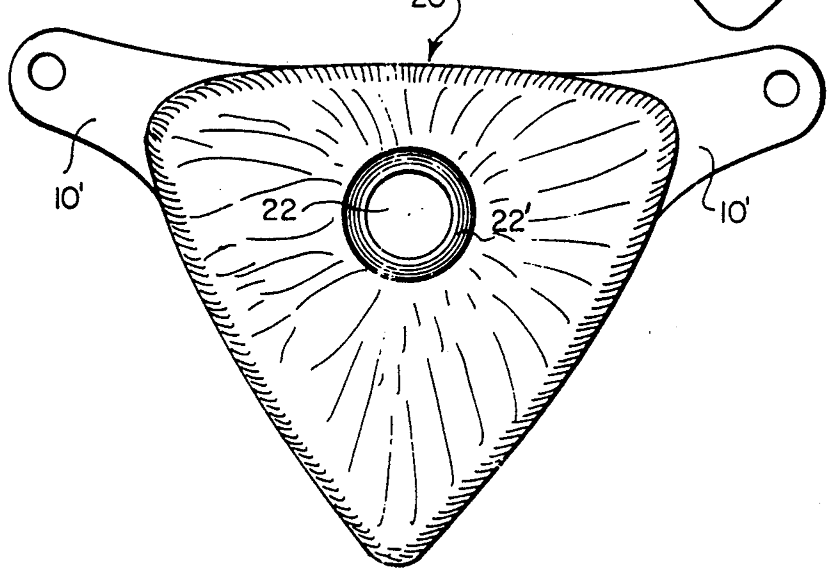
FIG. 3 is a rear view of the invention depicted in FIGS. 1 & 2.

The invention of this device comprises a "tracheostomy bubble" chamber having an external face 10 which is formed of semi-rigid bendable material, relative to the opposed inner barrier 20. Neck ties 10′ extend rearwardly therefrom. The outer barrier is of convex configuration and the pliable inner barrier is concave, the two elements being secured together by a cushion 10″ when joined. The outer external barrier 10 defines inhalation aperture 12 not shown and drainage aperture 12′, not shown, to which is adapted a drainage tube 12″. A housing 30 thereon secures adapter tube 32, the same likewise being swivel mounted thereon. This housing 30 which defines tubing adapter 32, attaches to the swivel 30′ and forms exhalation port 34. Exhalation port 34 is formed below the inhalation port 32. Vent holes 36 are formed along the top of the front face, giving atmospheric access to the interior between barriers 10 and 20. Located on the lowermost portion of the face 10 is a drainage aperture 12′ not shown and drainage tube 12″ connected thereto. See FIGS. 1 and 2.

In operation, the unit functions as follows: the tracheostomy bubble chamber is applied to the patient and secured to his/her neck by means of the removable elastic strap 40. Of course the tracheostomy tube having been affixed to the patient's trachea is carefully inserted through the adapter aperture 22 of the inner barrier 20, thus providing breathing access to the interior of the tracheostomy bubble chamber between its corresponding inner and outer barriers 10-20. Now the patient is given unimpeded breathing access to the atmosphere upon exhalation through valve 34 and, perforce inhalation access to humidified aerosol through the inhalation port 32. This is assuming that the unit 30 bearing the inhalation port 32 has been attached to a source of aerosol containing oxygen and/or a humidification spray. Clearly the location of the elements attached to and forming a part of the housing 30 may be rotated and/or elevated relative to the patient by means of the movable relationship best illustrated in FIG. 2. As will be apparent, the tube 12" will educt undesirable collection of fluids emanating from the patient's trachea.

In the rear barrier of the mask, the pliable rear face defines a tracheostomy tube adapter aperture 22 to which is secured an adapter 22'.

We claim:

1. A tracheostomy chamber unit adapted post-operatively to a tracheostomized patient, wherein the chamber defines a humidified and oxygenated interior, comprising:

a) a forwardly positioned curvilinear base forming a semi-rigid bendable convex external barrier upon which inhalation and exhalation ports are directly attached in the upper portion thereof and in which a suction accessible drainage port is likewise directly fixed in its lower portion;

b) a rearwardly positioned, pliable inner barrier, sealed in rearward spaced relation to the external barrier, said internal barrier defining in its upper portion a tracheostomy tube aperture passing therethrough, permitting access of a tracheostomy tube to the humidified and oxygenated interior of the chamber;

c) an aerosol housing secured in swivel connection to the external barrier, said housing having inhalation and exhalation port oppositely adjacent the tracheostomy tube aperture of the internal barrier, said drainage port located in the external barrier, beneath the aerosol housing in secretion and condensate collection relationship to respective external and internal barriers forming the chamber unit, thereby presenting suction access for the only procedurally acceptable withdrawal of secretions and condensate from the chamber.

2. The tracheostomy chamber unit of claim 1 wherein the external barrier has an arcuate in-line array of plural apertures above the aerosol housing to vent the chamber to the atmosphere.

* * * * *